United States Patent [19]

Jessel, Jr. et al.

[11] Plant 4,882

[45] Aug. 31, 1982

[54] CARNATION PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 175,753

[22] Filed: Aug. 5, 1980

[51] Int. Cl.[3] ..... A01H 5/00

[52] U.S. Cl. ..... Plt./73

[58] Field of Search ..... Plt./73

*Primary Examiner*—James R. Feyrer

*Attorney, Agent, or Firm*—Schwartz, Jeffery, Schwaab, Mack, Blumenthal & Koch

[57] ABSTRACT

A carnation plant known by the cultivar name Duke and particularly characterized as to uniqueness by the combined characteristics of commercial double flower type; flat flower form, twisting slightly with maturity; medium flower size; crimson red flower color with minimum color oxidation; medium flowering response; 4 to 6 flowers and buds showing color per flowering stem; medium peduncle length; strong peduncle strength; and tall plant height.

2 Drawing Figures

The present invention comprises a new and distinct cultivar of *Dianthus caryophyllus,* L., hereinafter referred to by the name Duke.

Duke is the product of a planned breeding program which had the objective of creating new spray type carnation cultivars in a wide color range with fast flowering response, unrestricted breaking action, vigorous growth, strong non-brittle stems, high bud and flower count, and attractive, durable flowers for year-round commercial production.

Duke was originated from a hybridization made in Barberton, Ohio in the year 1974 between two unnamed seedlings (#65070001 and #64019024).

Duke was discovered and selected as one flowering plant within a progeny of the stated parentage by Walter H. Jessel, Jr. and William E. Duffett on July 18, 1975 in a controlled environment in Barberton, Ohio.

The first act of asexual reproduction of Duke was accomplished when vegetative cuttings were taken from the initial selection in October, 1975 in a controlled environment in Barberton, Ohio by a technician working under formulations established and supervised by Walter H. Jessel, Jr. and William E. Duffett. Horticultural examination of selected units initiated June 13, 1977 has demonstrated that the combination of characteristics as herein disclosed for Duke are firmly fixed and are retained through successive generations of asexual reproduction.

Duke has not been observed under all possible environmental conditions. The phenotype may vary significantly with variations in environment such as temperature, light intensity and day length. The following observations, measurements and comparisons described plants grown in Barberton, Ohio and in Salinas, Calif. under greenhouse conditions which approximate those generally used in commercial practice.

The following traits have been repeatedly observed and are determined to be basic characteristics of Duke which in combination distinguish this carnation as a new and distinct cultivar:

(1) commercial double flower type;

(2) flat flower form, twisting slightly with maturity;

(3) medium flower size, ranging from 60 to 65 mm. in diameter;

(4) crimson red flower color with minimum color oxidation;

(5) medium flowering response;

(6) 4 to 6 flowers and buds showing color per flowering stem;

(7) medium peduncle length, ranging from 7 to 10 cm.;

(8) strong peduncle strength; and (9) tall plant height.

Of the several commercially available carnations known to the present inventors, the most similar in comparison to Duke are Elegance (unpatented) and Chieftain, disclosed in U.S. Plant Pat. No. 3,367. Reference is made to Chart A which compares selected characteristics of Elegance and Chieftain with the new cultivar. General comparisons are as follows:

(1) In comparison to Elegance, Duke has different flower color, larger flower size, and taller plant height. The number of buds and flowers per stem, flowering response period, peduncle length and peduncle strength of Duke are similar to those same characteristics of Elegance.

(2) In comparison to Chieftain, Duke has smaller flower size, shorter flowering response period and longer peduncle length. The flower color, number of buds and flowers per stem, peduncle strength and plant height of Duke are similar to those same characteristics of Chieftain.

In the accompanying photographic drawings, Sheet 1 is a color photograph showing typical inflorescence and foliage characteristics of Duke, and Sheet 2 is a black and white photograph showing three views of the inflorescence. Colors are as nearly true as possible with color illustrations of this type.

In the following description, color references are made to A Limit Color Cascade, by the Munsell Company, 1972 edition. Color values were determined between 8:00 a.m. and 8:30 a.m. on Sept. 14, 1979 under 100 foot-candle light intensity at Salinas, Calif.

Classification:

*Botanical.*—*Dianthus caryophyllus,* L. 'Duke'.

*Commercial.*—Spray carnation for cut flower production.

INFLORESCENCE CHARACTERISTICS

Flowering response: Fast, ranging from 17 weeks (at Salinas, Calif. grown pinched from a June 29 plant date) to 30 weeks (at Barberton, Ohio grown pinched from an October 22 plant date).

Inflorescence type: Terminal spray, with 4 to 6 buds per lateral.

Number of buds and flowers per stem: 4 to 6 showing color on first crop.

Peduncle length: Medium, ranging from 7 to 10 cm. on top flower.

Peduncle strength: Strong, holding flowers erect in all periods.

Flower:

*Size.*—Medium, 60 to 65 mm. in diameter when grown as a spray; too small for adoption as a commercial disbud.

*Type.*—Commercial double, petals from 20 to 25 in number.

*Form.*—Flat, twisting slightly with maturity.

Corolla: Smooth texture, both abaxial and adaxial; deeply serrated petal margin.

Corolla color:

*General tonality from a distance of* 3 meters.—Crimson red, 39-14 to 39-13.

*Abaxial.*—40-13 to 40-14.

*Adaxial.*—Approximately 39-14 but more greyed, to 41-12 but more greyed.

*Keeping quality.*—On plant, up to 18 days; as a cut flower up to 15 days under room temperature of 20° C.

*Fragrance.*—Very slight to none, typical carnation.

*Reproduction organs.*—Androecium: typical carnation, normal in all respects; long filament length, moderate to abundant pollen. Gynoecium: typical carnation, normal in all respects; white pistil of medium length, approximately 30 to 32 mm.

PLANT CHARACTERISTICS

Growth and duration: Bushy and vigorous semi-erect perennial typical of cultivars adaptable to commercial cut spray production, similar to that of Elegance.

Branching pattern: Semi-erect, numerous and unrestricted at base of plant.

Height: Tall, 75 to 80 cm. at time of first cut grown as a pinched plant.

Stem: Strong, with bend of 5 to 10 degrees (Society of American Florist's Standards), almost brittle during low light periods, approximately 50 to 55 cm. in length from top to first vegetative lateral.

Foliage:

*Occurrence.*—Abundant; typical carnation.

*Color (abaxial).*—Approximately 21-14 to 21-15 but more greyed.

*Color (adaxial).*—Approximately 21-13 to 21-14 but more greyed.

CHART A

COMPARISON OF DUKE, ELEGANCE, AND CHIEFTAIN

| CULTIVAR | FLOWER COLOR | FLOWER SIZE | NO. OF BUDS & FLOWERS PER STEM | FLOWERING RESPONSE PERIOD |
|---|---|---|---|---|
| DUKE | Crimson Red | Medium 60 to 65 mm | 4 to 6 | Fast, 17 to 30 weeks |
| ELEGANCE | White deep pink bicolor | Small 55 to 60 mm | 4 to 6 | Fast, 18 to 28 weeks |
| CHIEFTAIN | Crimson Red | Large 80 to 95 mm | 4 to 6 | Medium 22 to 30 weeks |

| CULTIVAR | PEDUNCLE LENGTH | PEDUNCLE STRENGTH | PLANT HEIGHT |
|---|---|---|---|
| DUKE | Medium 7 to 10 cm. | Strong | Tall 75 to 80 cm. |
| ELEGANCE | Medium 6 to 10 cm. | Strong | Medium 65 to 70 cm. |
| CHIEFTAIN | Short, 4 to 6 cm. | Strong | Tall 80 to 85 cm. |

COMPARISON MADE OF PINCHED, FLOWERING PLANT GROWN AS NATURAL SPRAYS IN BARBERTON, OHIO AND SALINAS, CALIFORNIA

We claim: /

1. A new and distinct cultivar of *Dianthus caryophyllus,* L. known by the cultivar name Duke, as described and illustrated, and particularly characterized as to uniqueness by the combined characteristics of commercial double flower type; flat flower form, twisting slightly with maturity; medium flower size, crimson red flower color with minimum color oxidation; fast flowering response; 4 to 6 flowers and buds showing color per flowering stem; medium peduncle length; strong peduncle strength; and tall plant height.

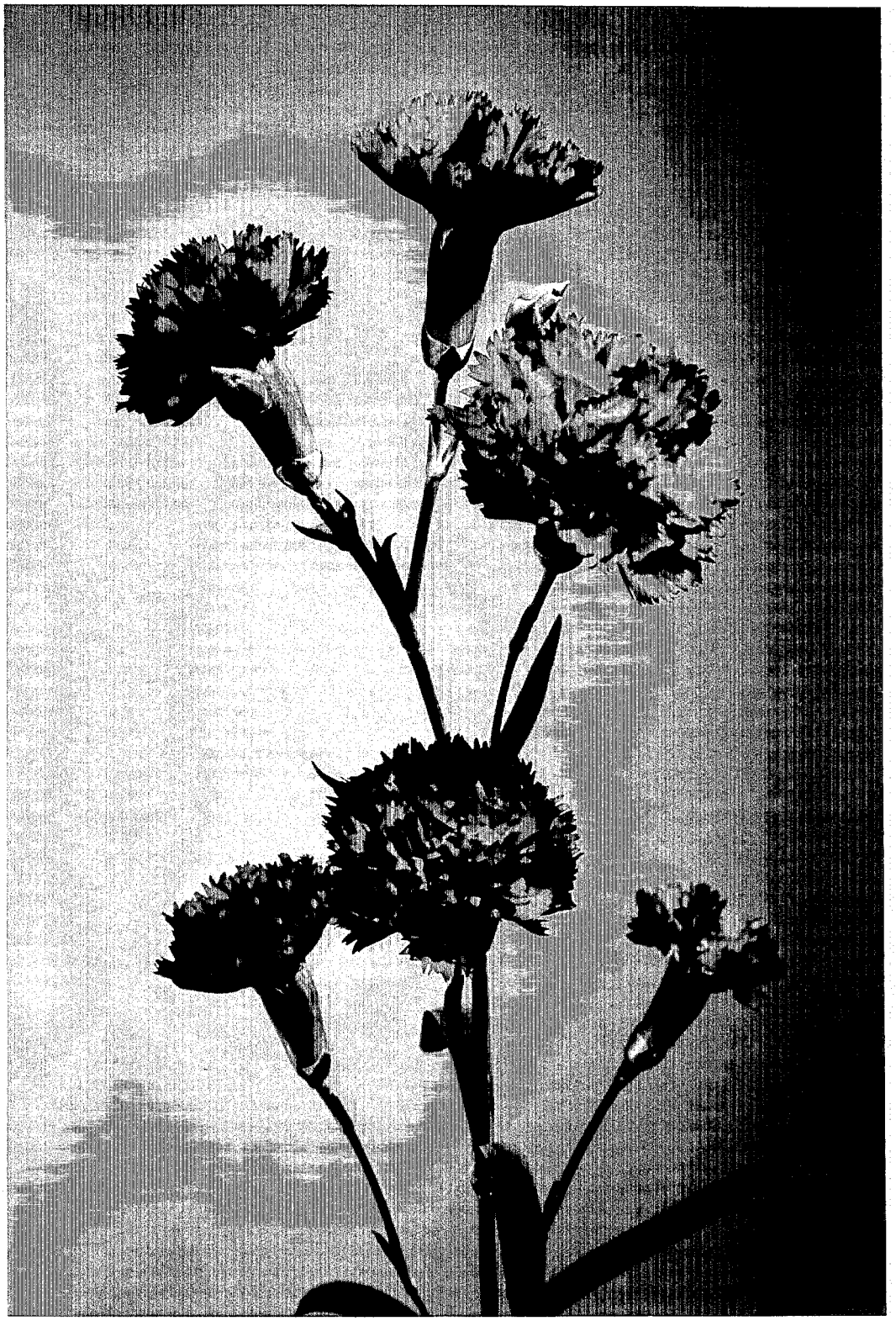

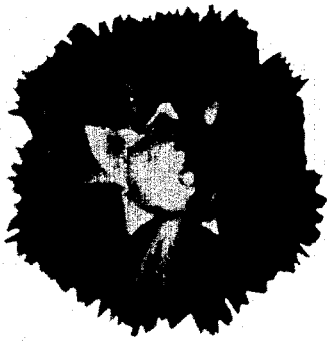
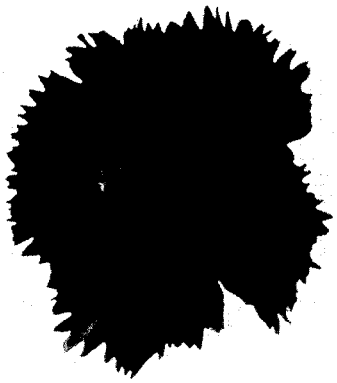
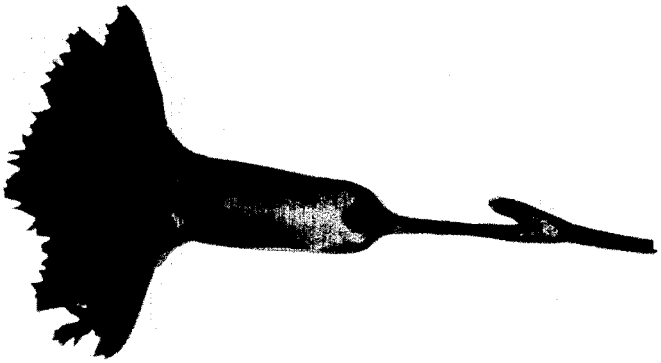

* * * * *